| United States Patent [19]
Ashton et al.

[11] 3,933,907
[45] *Jan. 20, 1976

[54] THIOPHOSPHORUS ACID AMIDES

[75] Inventors: Stanley Ashton; Vijay Ratna Sharma; John Anthony Taylor, all of Manchester, England

[73] Assignee: Imperial Chemical Industries Limited, London, England

[ * ] Notice: The portion of the term of this patent subsequent to Jan. 13, 1993, has been disclaimed.

[22] Filed: Jan. 17, 1974

[21] Appl. No.: 434,302

[30] Foreign Application Priority Data
Jan. 23, 1973 United Kingdom................. 3348/73

[52] U.S. Cl. ... 260/551 P; 260/465.5 R; 260/471 R; 260/543 P; 260/551 S; 260/557 R; 260/556 A; 260/556 AR; 260/558 R; 260/559 R; 260/561 R; 260/562 R; 260/780; 260/941; 260/944; 260/936; 260/940
[51] Int. Cl.²........................................ C07C 145/02
[58] Field of Search ........... 260/551, 947, 923, 941, 260/940, 465.5, 471, 543, 556–562, 944, 936

[56] References Cited
UNITED STATES PATENTS
3,755,507  8/1973  Brown................................ 260/947
FOREIGN PATENTS OR APPLICATIONS
1,022,587  6/1958  Germany ........................... 260/551

Primary Examiner—Harry I. Moatz
Attorney, Agent, or Firm—Cushman, Darby & Cushman

[57] ABSTRACT

Amides of phosphorus-containing thioacids are reacted with sulphenyl halides to give phosphorus-containing thioacid amides in which one or more of the nitrogen atoms carries a substituent attached through a sulphur atom. These substituted amides are inhibitors of premature vulcanisation in rubbers. The most effective compounds carry a secondary alkylthio or cycloalkylthio on each nitrogen atom.

6 Claims, No Drawings

THIOPHOSPHORUS ACID AMIDES

This invention relates to amides of phosphorothioic acids of value as inhibitors of premature vulcanisation in rubbers.

It is customary in the manufacture of vulcanised rubbers to incorporate into the unvulcanised rubber various additives such as antioxidants, antiozonants, fillers, vulcanisation activators, etc., and lastly vulcanisation accelerators and a vulcanising agent such as sulphur. The compounded rubber is then shaped and finally raised to vulcanisation temperature. Before the final stage, however, some premature vulcanisation may take place, especially during the compounding stage in a mill or Banbury mixer when heat is generated, or during handling such as calendering or extruding, or in some cases even during storage. Premature vulcanisation causes the rubber to become lumpy with the result that subsequent processing or vulcanising operations cannot be carried out satisfactorily. Premature vulcanisation may be reduced by using delayed action accelerators of for example the benzthiazylsulphenamide type and also by the use of retarders such as N-nitrosodiphenylamine or salicylic acid, but these retarders frequently introduce other difficulties. No satisfactory means of preventing premature vulcanisation has hitherto been found and the increasing use of furnace carbon blacks and of antioxidants and antiozonants based on p-phenylenediamine has exacerbated the problem. It has now been found that certain novel N-substituted amides of phosphorothioic acids are powerful inhibitors of premature vulcanisation.

According to the invention there are provided amides of the formula:

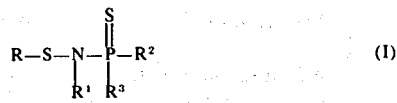

wherein R is an optionally substituted hydrocarbyl group, $R^1$ is a hydrogen atom, an optionally substituted hydrocarbyl group or a group of the formula $R^6$—CO—, $R^6$—$SO_2$— or

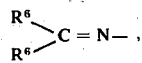

wherein $R^6$ is a hydrogen atom or a group R, and $R^2$ and $R^3$, which may be the same or different, are each a group R—S—$NR^1$—, a halogen atom or an optionally substituted alkyl, alkenyl, cycloalkyl, alkoxy, alkenoxy, cycloalkyloxy, aryl or aryloxy group or a substituted amino group or $R^2$ and $R^3$ together with the phosphorus atom form a heterocyclic ring or $R^1$ and $R^2$ together with the phosphorus and nitrogen atoms form a heterocyclic ring.

As examples of groups which may be represented by R or $R^1$ there are mentioned alkyl groups such as methyl, ethyl, propyl, isopropyl, butyl, isobutyl, tert-butyl, hexyl, n-octyl, tert-octyl, n-dodecyl, tert-dodecyl and n-octadecyl, alkenyl groups such as propenyl, n-but-1-enyl, isobutenyl, n-pent-1-enyl, dodecenyl and n-octadecenyl, cycloalkyl groups such as cyclopentyl and cyclohexyl, aryl groups such as phenyl, o-, m- and p-tolyl and naphthyl, and substituted hydrocarbyl groups such as β-methoxyethyl, alkyloxycarbonylethyl, β-cyanoethyl, 2-formylprop-2-yl, 4-chlorophenyl, 4-methoxyphenyl, 4-dimethylaminophenyl, 2-nitrophenyl, 4-nitrophenyl, 2,3,4,5,6-pentachlorophenyl, 2-methoxycarbonylphenyl and 4-phenylsulphonylphenyl.

As examples of groups which may be represented by $R^1$ there are also mentioned groups of the formula $R^6$—CO— or $R^6$—$SO_2$— wherein $R^6$ is especially an alkyl group such as a methyl group or an aryl group such as a phenyl or tolyl group, and alkylidene imine groups such as $CH_3$—CH=N—.

It is preferred that R be an alkyl group, especially a secondary alkyl, or a cycloalkyl group.

It is preferred that $R^1$ be an alkyl group such as a methyl or n-butyl group or a cycloalkyl group.

As a halogen atom which may be represented by $R^2$ or $R^3$ there is mentioned bromine and, especially, chlorine.

As examples of groups which may be represented by $R^2$ or $R^3$ there are mentioned the alkyl, alkenyl, cycloalkyl and aryl groups and substituted derivatives thereof which may be represented by R or $R^1$ and alkoxy, alkenyloxy, cycloalkyloxy, and aryloxy groups and substituted derivatives thereof derived from such groups.

As examples of substituted amino groups which may be represented by $R^2$ or $R^3$ there are mentioned ethylamino, diethylamino, dimethylamino, phenylamino, methylphenylamino and ethylphenylamino.

As examples of heterocyclic rings which may be formed from $R^2$ and $R^3$ together with the phosphorus atom there are mentioned 2-thiono-1,3,2-diazaphospholane, 2-thiono-4,5-benzo-1,3,2-diazaphospholane 2-thiono-1,3,2-oxazaphospholane and 2-thiono-4,5-benzo-1,3,2-oxazaphospholane.

As examples of heterocyclic rings which may be formed from $R^1$ and $R^2$ together with the phosphorus and nitrogen atoms there are mentioned 1,3,2-oxaza-2-thionophospholane and 1,3,2-diaza-2-thiono-4,5-benzophospholane.

As examples of amides of the invention there may be mentioned:

N,N',N''-trimethyl-N,N',N''-tris(isopropylthio)-phosphorothioic triamide,

N,N',N''-tri-n-butyl-N,N',N''-tris(cyclohexylthio)-phosphorothioic triamide,

N,N',N''-tricyclohexyl-N,N',N''-tris(isopropylthio)-phosphorothioic triamide,

N,N',N''-trimethyl-N,N',N''-tris(phenylthio)phosphorothioic triamide,

N,N',N''-triethyl-N,N',N''-tris(n-butylthio)phosphorothioic triamide,

N,N',N''-triphenyl-N,N',N''-tris(cyclohexylthio)-phosphorothioic triamide,

N,N',N''-trimethyl-N,N',N''-tris(t.-butylthio)phosphorothioic triamide,

N,N',N''-tri-n-butyl-N,N',N''-tris(benzylthio)phosphorothioic triamide,

N,N'-diethyl-N,N'-bis(isopropylthio)phosphorodiamidothioic chloride, 1,3-bis(phenylthio)-2-thiono-2-ethoxy-1,3,2-diazaphospholane, N,N'-diphenyl-N,N'-bis(4-methoxyphenylthio)phosphorodiamidothioic chloride O,N,N'-trimethyl-N,N'-bis(isopropylthio)phosphorodiamido thionate, O-methyl-N,N'-dicyclohexyl-N,N'-bis(2-chlorophenylthio)phosphorodiamido thionate, O-methyl-N,N'-di-n-butyl-N,N'-bis(chloromethylthio)phosporodiamido thionate,
O-phenyl-N,N'-dimethyl-N,N'-bis(methylthio)phosphorodiamido thionate,
N,N',N''-tris(n-dodecylthio)-2-thiono-2-phenylamino-1,3,2-diazaphospholane,
O,O',N-trimethyl-N-t,-hexadecylthiophosphoroamido thionate,
O,O',N-trimethyl-N-isopropylthiophosphoroamido thionate,
O,O'-dimethyl-N-cyclohexyl-N-isopropylthiophosphoroamido thionate,
O,O'-diethyl-N-n-butyl-N-cyclohexylthiophosphoroamido thionate,
O,O'-diethyl-N-benzyl-N-methylthiophosphoroamido thionate,
N,N'-dimethyl-N,N'-bis(isopropylthio)phenylphosphonothioic diamide,
N,N'-di-n-butyl-N,N'-bis(phenylthio)-p-tolylphosphorothioic diamide,
P,P,N-trimethyl-N-t.-butylthiophosphinothioic amide and
P,P,N-diphenyl-N-cyclohexyl-N-benzylthiophosphinothioic amide.

According to the invention there is also provided a process for the manufacture of amides of the formula I which comprises reacting a compound of the formula:

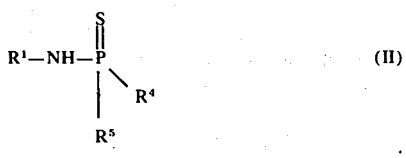

with a sulphenyl halide of the formula R—S—Halogen wherein $R^1$, $R^2$ and $R^3$ have the meanings given hereinbefore and $R^4$ and $R^5$ are each a group of the type represented by $R^2$ and $R^3$.

The process is conveniently carried out at a temperature preferably between $-10°$ and $100°C$, preferably in an inert solvent such as cyclohexane, carbon tetrachloride or toluene, and in presence of an acid binding agent such as pyridine, triethylamine, N,N-dimethylaniline or potassium carbonate.

The amount of sulphenyl halide, preferably sulphenyl chloride or bromide, is preferably about 1 molar proportion for each —$NHR^1$ group. In these circumstances a group $R^4$ or $R^5$ which represents a —$NHR^1$ group will be converted into a group —$NR^1$—SR. If a deficiency of sulphenyl halide is used only a corresponding proportion of the groups of the type —$NHR^1$ will be converted into groups —$NR^1$—SR.

The amide of formula I may be conveniently isolated by removal of most of the solvent under reduced pressure and crystallisation in the case of solids. Suitable solvents for crystallisation include alcohol, hexane, chloroform and toluene. Where the products are liquids purification is most readily effected by chromatography over silica gel or alumina.

As compounds of formula II which may be used in the process of the invention there may be mentioned phosphoric triamides, e.g.

N,N',N''-trimethylphosphorothioic triamide, phosphorothioic triamide,
N,N',N''-tri-n-butyl phosphorothioic triamide,
N,N',N''-tricyclohexyl phosphorothioic triamide,
N,N',N''-tri-t.-butyl phosphorothioic triamide,
N,N',N''-tri-n-dodecyl phosphorothioic triamide,
N,N',N''-triphenyl phosphorothioic triamide,
N,N'-dimethyl phosphorodiamidothioic chloride,
N,N'-di-n-butyl phosphorodiamidothioic chloride,
N,N'-di-cyclohexyl phosphorodiamidothioic chloride,
N,N'-diphenyl phosphorodiamidothioic chloride,
N,N'-di-n-hexadecyl phosphorodiamidothioic chloride,
N-methyl phosphoroamido thioic dichloride,
N-n-propyl phosphoroamidothioic dichloride,
N-t.-butyl phosphoroamidothioic dichloride,
N-phenyl phosphoroamidothioic dichloride,
O,N,N'-trimethyl phosphorodiamido thionate,
O-methyl-N,N'-dicyclohexyl phosphorodiamido thionate,
O-methyl-N,N'-diphenyl phosphorodiamido thionate,
O,N,N'-triethyl phosphorodiamido thionate,
O-ethyl-N,N'-diphenyl phosphorodiamido thionate,
O-ethyl-N,N-dicyclohexyl phosphorodiamido thionate,
O,N,N'-triphenyl phosphorodiamido thionate,
O,O',N-trimethyl phosphoramido thionate,
O,O'-dimethyl-N-n-butyl phosphoroamido thionate,
O,O'-dimethyl-N-cyclohexyl phosphoramido thionate,
O,O'-diethyl-N-phenyl phosphoramido thionate,
O,O'-diphenyl-N-methyl phosphoramido thionate,
O,O',N-triphenyl phosphoramido thionate,
N,N'-dimethyl-n-butyl phosphorothioic diamide,
N,N'-di-n-butyl methyl phosphorothioic diamide,
N,N'-dicyclohexyl phenylphosphorothioic diamide,
N,N'-diphenyl p-tolyl phosphorothioic diamide,
P,P,N-trimethyl phosphinothioic amide,
P,P-diphenyl-N-methyl phosphinothioic amide and
P,P,N-diphenyl-N-cyclohexyl phosphinothioic amide.

According to the invention there is further provided a process for reducing the premature vulcanisation of a rubber containing a vulcanising agent and a vulcanisation accelerator which comprises incorporating in the rubber an amide of the formula I.

The vulcanising agent used in this second process of the invention may be a sulphur donor, such as N,N'-dithiobismorpholine, N,N'-dithiobis-caprolactam, tetramethylthiuram disulphide, diethylthiophosphoryl disulphide or diethylthiophosphoryl trisulphide or preferably elemental sulphur, or for example a peroxide or other type of vulcanising agent.

The vulcanisation accelerator used in the second process of the invention is preferably a sulphenamide such as N-cyclohexylbenzothiazole-2-sulphenamide, N-t-butylbenzothiazole-2-sulphenamide, N-diethyleneoxybenzothiazole-2-sulphenamide or N-dicyclohexylbenzothiazole-2-sulphenamide, a thiazole such as mercaptothiazole, 2-mercaptobenzothiazole or dibenzothiazyl disulphide or a thiuram such as tetramethylthiuram monosulphide, tetramethylthiuram disulphide, tetramethylthiuram tetrasulphide, tetraethylthiuram monosulphide, tetraethylthiuram disulphide, or a metal salt of a dithiocarbamate such as zinc dimethyldithiocarbamide or sodium diethyldithiocarbamate.

Other types of accelerator may however be used such as diaryl guanidines, thioureas, xanthates or aldehyde-amine condensates, or mixtures of any of these and the above accelerators.

The amount of vulcanisation accelerator may be that conventionally used in the manufacture of rubber vulcanisates.

The amount of amide may be from 0.01 to 5% and preferably from 0.05 to 2.5% of the weight of the rubber.

Rubbers which may be used in the second process of the invention include both natural and synthetic rubbers and mixtures thereof. The synthetic rubber may in general be any polymeric material containing olefinic unsaturation and capable of being cross-linked by for example sulphur, peroxide or other cross-linking agents. Examples of synthetic rubbers include cis-polybutadiene, butyl rubber, ethylene-propylene terpolymer, polymers of 1,3-butadienes such as isoprene and chloroprene and copolymers of 1,3-butadiene with other monomers such as styrene, acrylonitrile and isobutylene.

The amide may be incorporated into the rubber mix by any conventional dry rubber or latex compounding procedure, for example on a rubber mill, in an internal mixer, through a screw type extruder blender, as a solution in an organic solvent or as an aqueous dispersion. The process of incorporation may be assisted if the amide is first blended with an inert inorganic diluent such as Fullers earth.

The rubber mix may also contain conventional rubber adjuvants such as antioxidants, antiozonants, fillers, peptising agents, pigments, blowing agents, and accelerator activators such as zinc oxide and stearic acid.

The invention is of particular value when the rubber mix is reinforced with a furnace black or contains a p-phenylene diamine-based antiozonant since such rubber mixes are especially prone to premature vulcanisation.

By the second process of the invention there are obtained vulcanisable rubber compositions which can be handled on conventional rubber processing machines or stored for long periods with little tendency to premature vulcanisation but which will cure readily at conventional vulcanisation temperatures to give vulcanisates of excellent physical properties. These unvulcanised rubber compositions, their vulcanisation by heating to vulcanisation temperatures, and the vulcanisates so obtained are further features of this invention.

The invention is illustrated but not limited by the following Examples in which all parts and percentages are by weight unless otherwise stated.

EXAMPLE 1

A solution of 16.55 parts of isopropyl sulphenyl chloride in 150 parts of carbon tetrachloride is added slowly to a stirred solution of 17.8 parts of N,N',N''-tricyclohexyl phosphorothioic triamide and 15.2 parts of triethylamine in 150 parts of carbon tetrachloride. After stirring for 30 minutes at 25°C the mixture is filtered and the solvent is removed under reduced pressure to leave a viscous yellow oil which on trituration with petroleum ether (b.p. 40°–60°C) gives 11.6 parts of N,N',N''-tris(isopropylthio)-N,N',N''-triscyclohexyl phosphorothioic triamide as a colourless solid melting at 125°–126°C. The n.m.r. spectrum is in accordance with the expected structure.

EXAMPLE 2

A solution of 18.9 parts of isopropyl sulphenyl chloride in 150 parts of carbon tetrachloride is added slowly to a stirred mixture of 16 parts of N,N',N''-tris-n-butyl phosphorothioic triamide and 17.1 parts of triethylamine in 150 parts of carbon tetrachloride. The mixture is filtered and the solvent is removed under reduced pressure to leave a yellow oil which is purified by chromatography over silica gel. Elution with chloroform gives 23 parts of N,N',N''-tris-isopropylthio-N,N',N''-tris-n-butyl phosphorothioic triamides as a pale yellow oil. The structure is confirmed by its n.m.r. and i.r. spectra.

EXAMPLE 3

A solution of 21.6 parts of isopropyl sulphenyl chloride in 150 parts of cyclohexane is added slowly to a stirred mixture of 25 parts of N,N',N''-tribenzyl phosphorothioic triamide and 20.2 parts of triethylamine in 100 parts of cyclohexane. After stirring for 30 minutes at 25°C the mixture is filtered and the solvent removed under reduced pressure to leave a viscous yellow oil which is purified by chromatography over silica gel. Elution with chloroform gives a colourless oil which on trituration with petroleum ether (b.p. 40°–60°C) gives 5.6 parts of N,N',N''-tris (isopropylthio)-N,N',N''-tribenzyl phosphorothioic triamide as a colourless solid melting at 92°–93°C. The structure expected is confirmed by n.m.r. spectroscopy.

EXAMPLE 4

|  | Parts by weight |
|---|---|
| Natural Rubber (Smoked Sheets) | 100 |
| Zinc Oxide | 3.5 |
| Stearic acid | 3 |
| High Abrasion Furnace Black | 45 |
| Process Oil | 3.5 |
| Sulphur | 2.5 |
| N-Cyclohexyl-2-benzthiazyl sulphenamide | 0.5 |
| Retarder | As given below |

The above ingredients were mixed on a 2-roll laboratory rubber mill in conventional manner and the mixed sheet stock was treated for scorch characteristics in a Mooney rotating disc plastometer and for cure characteristics in an oscillating disc Rheometer. The results are tabulated in Table 1.

| RETARDER | Mooney Scorch Minimum +10 (Minutes at 120°C) | RHEOMETER CURE CHARACTERISTICS AT 150°C | | |
|---|---|---|---|---|
| | | Induction time $T_2$ (Minutes) | Torque at 95% Peak (inch lbs) | Time to reach 95% Peak Torque (Minutes) |
| None | 23.5 | 6.4 | 74.5 | 19.3 |
| 0.3 parts of N,N',N''-tri-isopropylthio N,N',N''-tribenzylphosphorothioic triamide | 54 | 10.3 | 61 | 21.3 |
| 0.6 parts " | 58.4 | 11.9 | 74.8 | 25 |
| 0.25 parts of N,N',N''-tri-isopropylthio N,N',N''-n-butylphosphorothioic triamide | 47.5 | 9.1 | 70.7 | 22.7 |
| 0.25 parts of O,O'-dimethyl-N-cyclohexyl-N-isopropylthiophsophoramido thionate | 28 | 7.4 | 69.5 | 22.6 |
| 0.25 parts of N,N',N''-triallyl-N,N',N''-tris(isopropylthio)phosphorothioic triamide | 47 | 9.8 | 67 | 23.5 |

EXAMPLE 5

Using the same basic rubber composition as in preceding example Mooney scorch data was obtained at 130°C for the following retarders:

| Retarder | Mooney scorch at 130°C Minimum +10 (Minutes) |
| --- | --- |
| None | 11 |
| 0.25 parts of N,N',N''-tri-isopropylthio-N,N',N''-tricyclohexyl phosphorothioic triamide | 19 |
| 0.25 parts of N,N',N''-tribenzylthio-N,N',N''-tricyclohexyl phosphorothioic triamide | 14.5 |
| 0.25 parts of O,O'-dimethyl-N-phenylthio-N-cyclohexylphosphoramidothionate | 14 |
| 0.25 parts of N,N',N''-trimethyl-N,N',N''-tris(isopropylthio)phosphorothioic triamide | 18 |
| 0.25 parts of O,O'-dimethyl-N-isopropylthio-N-n-butylphosphoramidothionate | 18 |

EXAMPLE 6

A solution of 7.25 parts of phenylsulphenyl chloride in 50 parts of cyclohexane is added to a stirred solution of 11.15 parts of O,O'-dimethyl-N-cyclohexylphosphoramidothionate and 8 parts of triethylamine in 50 parts of cyclohexane. After stirring for 1 hour at room temperature the solid is removed by filtration, the filtrate collected and solvent removed under reduced pressure to leave an oil which is purified by chromatography over silica gel. Elution with chloroform gives 2.8 parts of o,o'-dimethyl-N-phenylthio-N-cyclohexylphosphoramidothionate as a colourless solid m.p. 68°–69°C.

EXAMPLE 7

A solution of 23.78 parts of benzyl sulphonyl chloride in 150 parts of cyclohexane is added slowly to a stirred suspension of 17.65 parts of N,N',N''-tricyclohexyl phosphorothioic triamide and 15.15 parts of triethylamine in 150 parts of cyclohexane. After stirring for 1 hour the mixture is filtered and the solvent is removed under reduced pressure to leave a red oil, which is purified by chromatography over silica gel. Elution with chloroform gives 22.2 parts of N,N',N''-tricyclohexyl-N,N',N''-tribenzylthiophosphorothioic triamide as a red oil.

EXAMPLE 8

A solution of 33.1 parts of isopropylsulphenyl chloride in 100 parts of cyclohexane is slowly added to a stirred solution of 15.3 parts of N,N',N''-trimethylphosphorothioic triamide and 30.3 parts of triethylamine in 200 parts of cyclohexane. After stirring for 1 hour solid is removed by filtration and solvent evaporated from the filtrate under reduced pressure to leave a red oil which is purified by chromatography over silica gel. Elution with chloroform gives 2.63 parts of N,N',N''-trimethyl-N,N',N''-triisopropylthiophosphorothioic triamide. The structure is confirmed by i.r. and n.m.r spectra.

EXAMPLE 9

A solution of 33.1 parts of isopropyl sulphenyl chloride in 150 parts of cyclohexane is added slowly to a stirred solution of 23.1 parts of N,N',N''-triallylphosphorothioic triamide and 30.3 parts of triethylamine in 150 parts of cyclohexane. After stirring for a further 1 hour at ambient temperature the mixture is filtered and the solvent removed at reduced pressure to leave a yellow oil which is purified by chromatography over silica gel. Elution with chloroform gives 24.5 parts of N,N',N''-triallyl-N,N',N''-tris(isopropylthio)phosphorothioic triamide as a colourless oil. The n.m.r. and i.r. spectra are in accord with the expected structure.

EXAMPLE 10

A solution of 5.50 parts of isopropylsulphenyl chloride in cyclohexane (100 parts) is added dropwise to a stirred mixture of O,O'-dimethyl-N-n-butylphosphoramidothionate (9.85 parts) and triethylamine (6.0 parts) in cyclohexane (100 parts). Triethylamine hydrochloride is filtered off and the filtrate evaporated under reduced pressure to leave 11.5 parts of O,O'-dimethyl-N-isopropylthio-N-n-butylphosphoramidothionate as a colourless oil.

EXAMPLE 11

A solution of 5.50 parts of isopropylsulphenyl chloride in 50 parts of cyclohexane is added to a stirred suspension of O,O'-dimethyl-N-cyclohexylphosphoramidothionate (11.15 parts) and triethylamine (6 parts) in cyclohexane (50 parts). When the addition is complete triethylamine hydrochloride is removed by filtration and the filtrate evaporated under reduced pressure to leave a sticky solid which on crystallisation from petroleum ether (b.p. 40°–60°) gives O,O'-dimethyl-N-isopropylthio-N-cyclohexylphosphoramidothionate (3.2 parts) as a colourless solid m.p. 34°C.

We claim:
1. An amide of the formula:

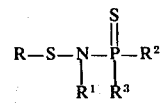

wherein R is alkyl of up to 18 carbon atoms, alkenyl of up to 18 carbon atoms, cycloalkyl containing 5–6 carbon atoms, phenyl, naphthyl, tolyl, β-methoxyethyl, β-cyanoethyl, 2-formylprop-2-yl, 4-chlorophenyl, 4-methoxyphenyl, 4-dimethylaminophenyl, 2-nitrophenyl, 4-nitrophenyl, 2,3,4,5,6-pentachlorophenyl, 2-methoxycarbonylphenyl or 4-phenylsulphonylphenyl, $R^1$ is hydrogen, alkyl of up to 18 carbon atoms, alkenyl of up to 18 carbon atoms, cycloalkyl containing 5–6 carbon atoms, phenyl, naphthyl, tolyl, β-methoxyethyl, β-cyanoethyl, 2-formylprop-2-yl, 4-chlorophenyl, 4-methoxyphenyl, 4-dimethylaminophenyl, 2-nitrophenyl, 4-nitrophenyl, 2,3,4,5,6-pentachlorophenyl, 2-methoxycarbonylphenyl or 4-phenylsulphonylphenyl or a group of the formula

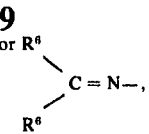

wherein $R^6$ is hydrogen or one of the values of R given above, one of $R^2$ and $R^3$ is $R — S — NR^1 —$ and the other is $R — S — NR^1 —$, halogen, a value as recited for R or —OR wherein R and $R^1$, in each instance, have the meaning given above.

2. An amide according to claim 1 wherein R is a secondary alkyl or cycloalkyl and $R^1$ is alkyl or cycloalkyl.

3. An amide according to claim 1 wherein both $R^2$ and $R^3$ are $R — S — NR^1 —$.

4. An amide according to claim 1 wherein R is methyl, ethyl, propyl, isopropyl, butyl, isobutyl, tert-butyl, hexyl, n-octyl, tert-octyl, n-dodecyl, tert-dodecyl, n-octadecyl, propenyl, n-but-1-enyl, isobutenyl, n-pent-1-enyl, dodecenyl, n-octadecenyl, cyclopentyl, cyclohexyl, phenyl, o-, m- and p-tolyl, naphthyl, β-methoxyethyl, β-cyanoethyl, 2-formylprop-2-yl, 4-chlorophenyl, 4-methoxyphenyl, 4-dimethylaminophenyl, 2-nitrophenyl, 4-nitrophenyl, 2,3,4,5,6-pentachlorophenyl, 2-methoxycarbonylphenyl or 4-phenylsulphonylphenyl; $R^1$ is hydrogen, one of the values recited for R, $CH_3—CH=N—$, $R^6—CO—$ or $R^6—SO_2—$ wherein $R^6$ is hydrogen, methyl, phenyl or tolyl and both $R^2$ and $R^3$ are $R — S — NR^1 —$.

5. An amide selected from the group consisting of
N,N',N''-trimethyl-N,N',N''-tris(isopropylthio)-phosphorothioic triamide,
N,N',N''-tri-n-butyl-N,N',N''-tris(cyclohexylthio)-phosphorothioic triamide,
N,N',N''-tricyclohexyl-N,N',N''-tris(isopropylthio)-phosphorothioic triamide
N,N',N''-trimethyl-N,N',N''-tris(phenylthio)phosphorothioic triamide,
N,N',N''-triethyl-N,N',N''-tris(n-butylthio)phosphorothioic triamide,
N,N',N''-triphenyl-N,N',N''-tris(cyclohexylthio)-phosphorothioic triamide,
N,N',N''-trimethyl-N,N',N''-tris(t.-butylthio)phosphorothioic triamide,
N,N',N''-tri-n-butyl-N,N',N''-tris(benzylthio)phosphorothioic triamide,
N,N'-diethyl-N,N'-bis(isopropylthio)phosphorodiamidothioic chloride,
1,3-bis(phenylthio)-2-thiono-2-ethoxy-1,3,2-diazaphospholane,
N,N'-diphenyl-N,N'-bis(4-methoxyphenylthio)phosphorodiamidothioic chloride
O,N,N'-trimethyl-N,N'-bis(isopropylthio)phosphorodiamido thionate,
O-methyl-N,N'-dicyclohexyl-N,N'-bis(2-chlorophenylthio)phosphorodiamido thionate,
O-methyl-N,N'-di-n-butyl-N,N'-bis(chloromethylthio)phosphorodiamido thionate,
O-phenyl-N,N'-dimethyl-N,N'-bis(methylthio)phosphorodiamido thionate,
N,N',N''-tris(n-dodecylthio)-2-thiono-2-phenylamino-1,3,2-diazaphospholane.
O,O'-dimethyl-N-cyclohexyl-N-isopropylthiophosphoroamido thionate,
O,O'-diethyl-N-n-butyl-N-cyclohexylthiophosphoroamido thionate,
O,O'-diethyl-N-benzyl-N-methylthiophosphoroamido thionate,
N,N'-dimethyl-N,N'-bis(isopropylthio)phenylphosphonothioic diamide,
N,N'-di-n-butyl-N,N'-bis(phenylthio)-p-tolylphosphorothioic diamide,
P,P,N-drimethyl-N-t.-butylthiophosphinothioic amide and
P,P,N-diphenyl-N-cyclohexyl-N-benzylthiophosphinothioic amide.

6. The amide of claim 1 which is N, N', N''-tris (isopropylthio)-N,N',N''-tris cyclohexyl phosphorothioic triamide.

* * * * *